United States Patent
Klemm et al.

(10) Patent No.: US 10,169,536 B2
(45) Date of Patent: Jan. 1, 2019

(54) RECORDING DOSE DATA FROM DRUG INJECTION DEVICES USING OPTICAL CHARACTER RECOGNITION (OCR)

(71) Applicant: SANOFI-AVENTIS DEUTSCHLAND GMBH, Frankfurt am Main (DE)

(72) Inventors: Thomas Klemm, Frankfurt (DE); Dietmar Hammen, Frankfurt (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/520,057

(22) PCT Filed: Oct. 15, 2015

(86) PCT No.: PCT/EP2015/073858
§ 371 (c)(1),
(2) Date: Apr. 18, 2017

(87) PCT Pub. No.: WO2016/062604
PCT Pub. Date: Apr. 28, 2016

(65) Prior Publication Data
US 2017/0316158 A1    Nov. 2, 2017

(30) Foreign Application Priority Data

Oct. 21, 2014 (EP) .................................. 14189705

(51) Int. Cl.
*G06K 7/10* (2006.01)
*G06F 19/00* (2018.01)
(Continued)

(52) U.S. Cl.
CPC ............. *G06F 19/321* (2013.01); *A61M 5/24* (2013.01); *A61M 5/315* (2013.01);
(Continued)

(58) Field of Classification Search
CPC ....... G06F 19/321; A61M 5/24; A61M 5/315; G06K 9/32; G06T 5/50; H04N 5/235
(Continued)

(56) References Cited

U.S. PATENT DOCUMENTS 5,126,544 A * 6/1992 Izumi .................. G06K 7/0166
235/454
5,523,552 A * 6/1996 Shellhammer ..... G06K 7/10871
235/462.09
(Continued)

FOREIGN PATENT DOCUMENTS

WO    WO 2013/045506    4/2013
WO    WO 2013/120774    8/2013

OTHER PUBLICATIONS

International Preliminary Report on Patentability in International Application No. PCT/EP2015/073858, dated Apr. 25, 2017, 8 pages.
(Continued)

*Primary Examiner* — Karl D Frech
(74) *Attorney, Agent, or Firm* — Fish & Richardson P.C.

(57) ABSTRACT

A method of recording a medicament dose using a data collection device comprises capturing an image of a medicament dose indicator of a medicament delivery device, adjusting a scale of said image, adjusting said image for skew of one or more characters displayed by the medicament dose indicator, determining the position of at least one of said one or more characters in the image, identifying the at least one character using optical character recognition and determining a medicament dose indicator by the medicament dose indicator based on a result of the optical character recognition. The method may be performed using a handheld electronic device comprising a camera, such as a cellphone, a tablet computer or other device. A computer program for controlling a data collection device to perform
(Continued)

the method may be provided in the form of a software application or "app".

17 Claims, 7 Drawing Sheets

(51) Int. Cl.
    *A61M 5/24*     (2006.01)
    *A61M 5/315*     (2006.01)
    *G06K 9/32*     (2006.01)
    *G06T 5/50*     (2006.01)
    *H04N 5/235*     (2006.01)
    *A61M 5/31*     (2006.01)
    *H04N 5/232*     (2006.01)

(52) U.S. Cl.
    CPC ......... *A61M 5/31525* (2013.01); *G06F 19/00* (2013.01); *G06F 19/3468* (2013.01); *G06K 9/32* (2013.01); *G06K 9/3283* (2013.01); *G06T 5/50* (2013.01); *H04N 5/235* (2013.01); *A61M 2005/3126* (2013.01); *A61M 2205/3306* (2013.01); *A61M 2205/505* (2013.01); *A61M 2205/52* (2013.01); *A61M 2205/6081* (2013.01); *H04N 5/23229* (2013.01)

(58) Field of Classification Search
    USPC .................................. 235/462.04, 462.13
    See application file for complete search history.

(56) References Cited

U.S. PATENT DOCUMENTS

| | | | | |
|---|---|---|---|---|
| 5,557,091 A * | 9/1996 | Krummel | ................. | G06K 7/14 |
| | | | | 235/462.08 |
| 7,946,493 B2 * | 5/2011 | Havens | .............. | G06K 7/10881 |
| | | | | 235/381 |
| 8,340,428 B2 * | 12/2012 | Perronnin | ............ | G06K 9/6255 |
| | | | | 382/186 |
| 9,093,072 B2 * | 7/2015 | Bathiche | ................. | G10L 15/24 |
| 9,098,611 B2 | 8/2015 | Pinter | | |
| 9,327,082 B2 | 5/2016 | Kouyoumjian | | |
| 2003/0076408 A1 | 4/2003 | Dutta | | |
| 2004/0069044 A1 | 4/2004 | Lavi | | |
| 2005/0171476 A1 | 8/2005 | Judson | | |
| 2006/0071950 A1 | 4/2006 | Kurzweil et al. | | |
| 2007/0060894 A1 | 3/2007 | Dai | | |
| 2007/0191784 A1 | 8/2007 | Jacobs | | |
| 2011/0118700 A1 | 5/2011 | Remde | | |
| 2011/0295215 A1 | 12/2011 | Nielsen et al. | | |
| 2012/0134588 A1 | 5/2012 | Zhang et al. | | |
| 2013/0197445 A1 * | 8/2013 | Schabbach | ......... | A61B 5/14532 |
| | | | | 604/189 |
| 2013/0314593 A1 | 11/2013 | Reznik | | |
| 2014/0005950 A1 | 1/2014 | Groeschke et al. | | |
| 2014/0232904 A1 | 8/2014 | Na et al. | | |
| 2016/0129182 A1 | 5/2016 | Schuster | | |
| 2016/0166766 A1 | 6/2016 | Schuster | | |

OTHER PUBLICATIONS

International Search Report and Written Opinion in International Application No. PCT/EP2015/073858, dated Jan. 14, 2016, 9 pages.
Piksoft Inc: "Perfect OCR: document scanner with high quality OCR on the App store on iTunes," Oct. 24, 2011, Retrieved from the Internet: URL: https://itunes.apple.com/us/app/perfect-ocr-document-scanner/id363095388?mt8.
"Datenbrillen:Erfolg durch intelligente Anwendungen in Unternehem," Technik and Wirtschaft, Nov. 2013, 1 page.
International Preliminary Report on Patentability in International Application No. PCT/EP2015/073860, dated Apr. 25, 2017, 9 pages.
International Search Report and Written Opinion in International Application No. PCT/EP2015/073860, dated Jan. 27, 2016, 13 pages.

* cited by examiner

RECORDING DOSE DATA FROM DRUG INJECTION DEVICES USING OPTICAL CHARACTER RECOGNITION (OCR)

CROSS-REFERENCE TO RELATED APPLICATIONS

This application is a U.S. national stage application under 35 USC § 371 of International Application No. PCT/EP2015/073858, filed on Oct. 15, 2015, which claims priority to European Patent Application No. 14189705.8 filed on Oct. 21, 2014, the entire contents of which are incorporated herein by reference.

TECHNICAL FIELD

The present disclosure relates to data collection from a medicament delivery device. In particular, the present disclosure relates to a method and a data collection device for recording a medicament dose.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dosage window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, for example, one or more of the injected insulin type, dose and timing of the injection, in a manner that is reliable and accurate.

Data collection techniques may also be used for purposes other than monitoring insulin injections. For example, data may be collected in order to monitor injections of other medicaments, other medical activities, such as the taking of tablet medication by a patient or infusions, or for non-medical purposes, such as the monitoring of equipment and/or its operation in a home or industrial environment for safety reasons.

SUMMARY

According to one aspect, there is provided a method of recording a medicament dose by a data collection device, the method including capturing, by a camera of the data collection device, an image of a medicament dose indicator of a medicament delivery device, adjusting a scale of said image, adjusting said image for skew of one or more characters displayed by said medicament dose indicator, determining the position of at least one of the one or more characters in the image, identifying the at least one character using optical character recognition and determining a medicament dose indicated by the medicament dose indicator based on a result of the optical character recognition.

The data collection device may be a handheld electronic device that includes a camera, such as a cellphone, a tablet computer, a PDA or similar device. Such devices are commonly available. Hence, medicament delivery may be recorded and monitored without requiring specialized, or dedicated, data collection devices. Also, since the user can utilize a device that is familiar to them for data collection, the user may begin to record dosages without having to familiarize themselves, and learn to use, a new device.

Said capturing of the image may include combining multiple images having different exposure levels to provide said image with a high dynamic range. The obtaining of such a high dynamic range image may provide a higher quality image and/or improved contrast, facilitating optical character recognition of the at least one character.

The method may also include obtaining color information from said image and identifying a type of medicament to be dispensed based on said color information. The obtaining of color information may, optionally, include determining a color balance measurement based on reference color information provided on the medicament delivery device. This may allow information regarding medicament type to be obtained automatically, without specific input from the user, potentially improving reliability of the information obtained.

The medicament delivery device may be an injector pen that includes a movable component for selecting said amount of medicament to be dispensed.

This aspect also provides a computer program including computer-readable instructions that, when executed by a processor, causes any of the above methods to be performed.

Such a computer program may be provided in, for example, a smartphone software application ("app") or an "app" for a tablet computer.

This aspect also provides a data collection device including a camera and a processing arrangement configured to capture an image of a medicament dose indicator of a medicament delivery device using said camera, adjust a scale of said image, adjusting said image for skew of one or more characters displayed by said medicament dose indicator, determine the position of at least one of the one or more characters in the image, identify the at least one character using optical character recognition and determine a medicament dose indicated by the medicament dose indicator based on a result of said optical character recognition.

The data collection device may be a handheld electronic device such as a cellphone or tablet computer.

The processing arrangement may be configured to capture the image by combining multiple images captured by said camera having different exposure levels to provide said image with a high dynamic range.

The processing arrangement may be configured to identify a color of at least one component of the medicament delivery device and to determine a type of said medicament based on said color. In some embodiments, the processing arrangement may be configured to obtain a color balance measurement based on an image showing reference color information provided on the medicament delivery device.

BRIEF DESCRIPTION OF THE FIGURES

Example embodiments of the subject matter described herein will now be described with reference to the accompanying figures, of which:

FIG. 1b shows a perspective view of some detail of the drug delivery device of FIG. 1a;

DETAILED DESCRIPTION

In the following, embodiments will be described with reference to an insulin injection device. The present disclosure is however not limited to such application and, as noted herein above, may equally well be deployed with injection devices that eject other medicaments, with other types of medicament delivery devices.

Figure 1A:
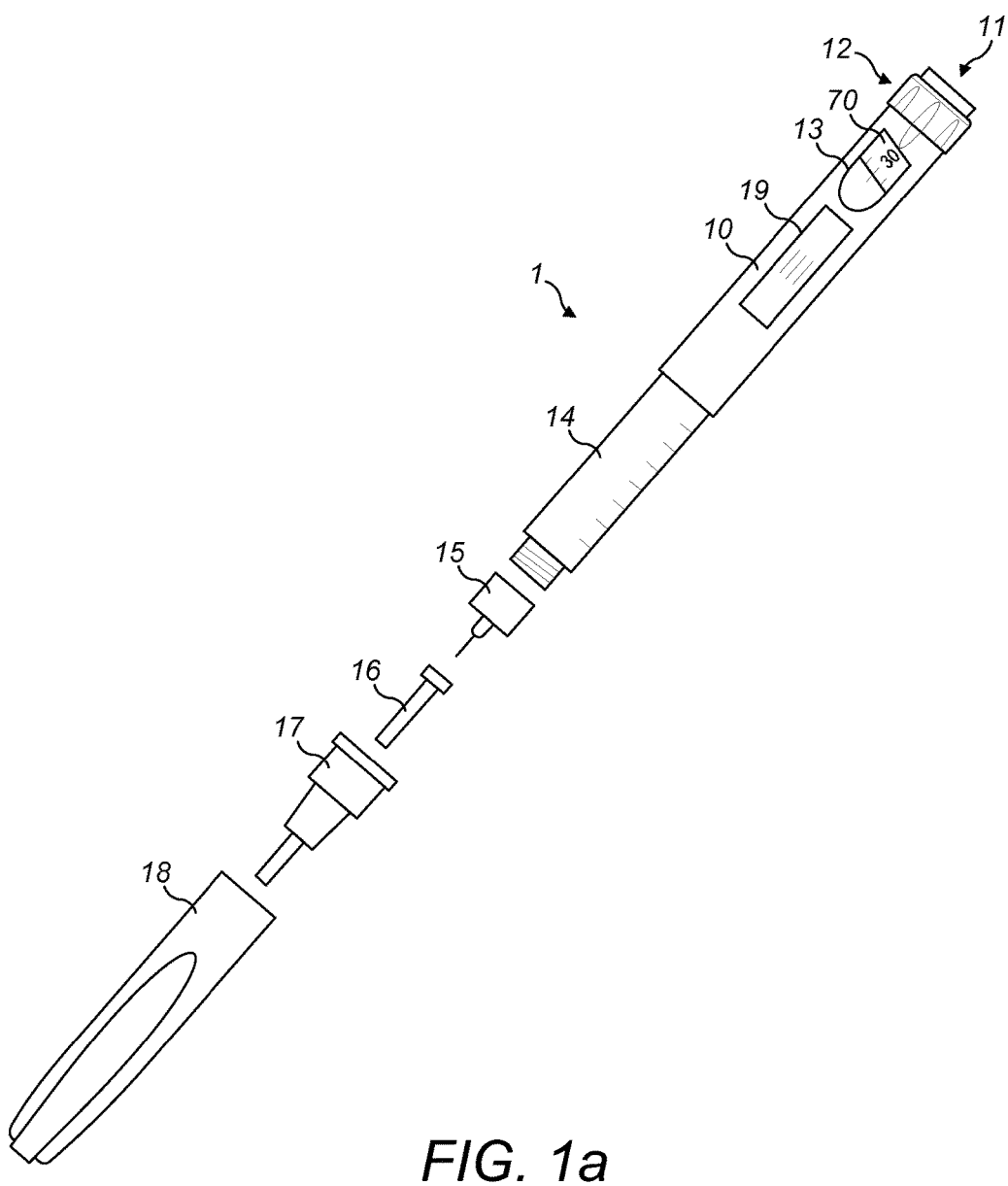
FIG. 1a shows an exploded view of a drug delivery device.

FIG. 1a is an exploded view of a medicament delivery device. In this example, the medicament delivery device is an injection device 1, such as Sanofi's SoloSTAR® insulin injection pen.

The injection device 1 of FIG. 1a is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently.

The dosage window 13 may be in the form of an aperture in the housing 10, which permits a user to view a limited portion of a number sleeve 70 that is configured to move when the dosage knob 12 is turned. In order to facilitate taking images of the numbers displayed in the dosage window 13, the number sleeve 70 may have a matte surface.

A label 19 is provided on the housing 10. The label 19 includes information about the medicament included within the injection device, including information identifying the medicament. The information identifying the medicament may be in the form of text. The information identifying the medicament may also be in the form of a color. For example, the label 19 may have a background, or include a shaded element such as a border having a color that corresponds to a particular type of medicament that is provided in the injection device. Alternatively, or additionally, the label may include a RFID tag or similar device that stores such information.

Optionally, one or more parts of the injection device, such as an injection button 11 or the dosage knob 12, may be formed of a material having a color that corresponds to the medicament. Optionally, a part of an insulin container (not shown) within the injection device 1 may include a color-coded portion that indicates a medicament type and may be viewable through the dosage window 13. The information identifying the medicament may additionally, or alternatively, be encoded into a barcode, QR code or the like. The information identifying the medicament may also be in the form of a black and white pattern, a color pattern or shading.

Turning the dosage knob 12 causes a mechanical click sound to provide acoustic feedback to a user. The numbered sleeve 70 mechanically interacts with a piston in insulin container 14. When needle 15 is stuck into a skin portion of a patient, and then injection button 11 is pushed, the insulin dose displayed in the dosage window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
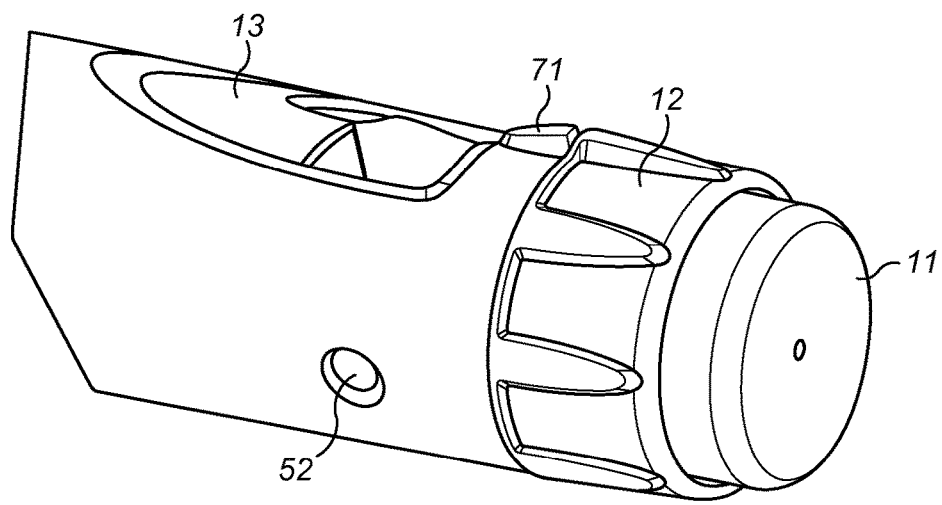

FIG. 1b is a close-up of the end of the injection device 1, showing a locating rib 71 that is located between the viewing window 13 and the dosage knob 12.

Figure 2A:
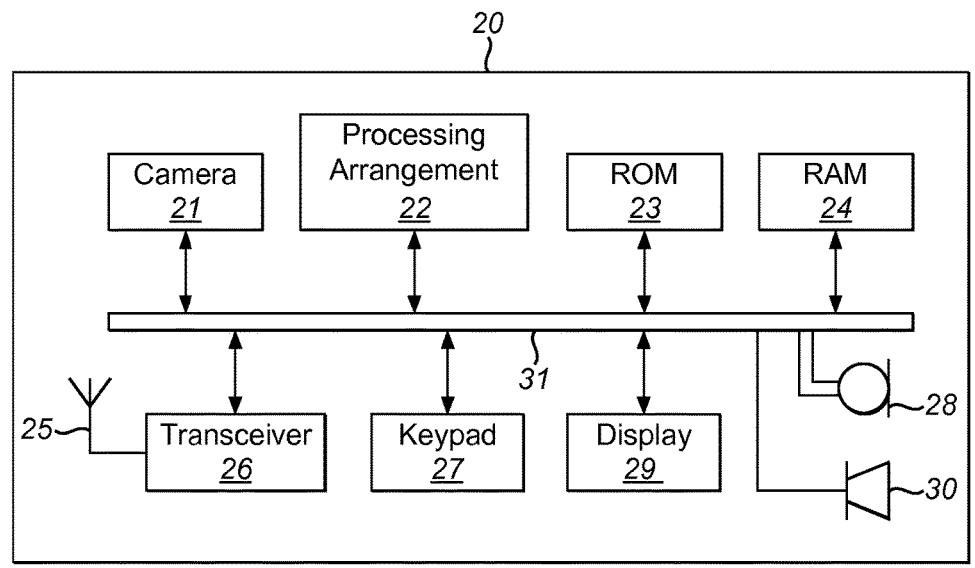
FIG. 2a is a block diagram of a data collection device according to an embodiment.

FIG. 2a is a block diagram of a data collection device according to an embodiment, that may be used to collect data, such as insulin type, dosage and timing of injection, from the injection device 1 of FIG. 1.

In the particular example shown in FIG. 2a, the data collection device is a cellphone 20, or "smartphone", equipped with a built-in camera 21, and a processing arrangement 22 including one or more processors, such as a microprocessor, a Digital Signal Processor (DSP), Application Specific Integrated Circuit (ASIC), Field Programmable Gate Array (FPGA) or the like. The cellphone 20 also includes memory units 23, 24, including a read-only memory 23 and a random access memory 24, which can store software for execution by the processing arrangement 22. The cellphone 20 also includes communications equipment 25, 26, such as an antenna 25 and a transceiver 26, to permit bi-directional communication with one or more of a cellphone network, a personal area network, a local wireless network and the Internet. The cellphone 20 further includes an input arrangement 27, 28, such as a keypad 27 and microphone 28, and an output arrangement 29, 30, such as a speaker 29 and display 30. In some embodiments, the input arrangement 27, 28 may include provide a keypad 27 in the form of part of a touch-screen that utilizes some or all of the display 30. The cellphone 20 also includes a communications bus 31 allowing for communication between the camera 21, processing arrangement 22, memory units 23, 24, communications equipment 25, 26, input arrangement 27, 28 and output arrangement 29, 30.

Figure 2B:
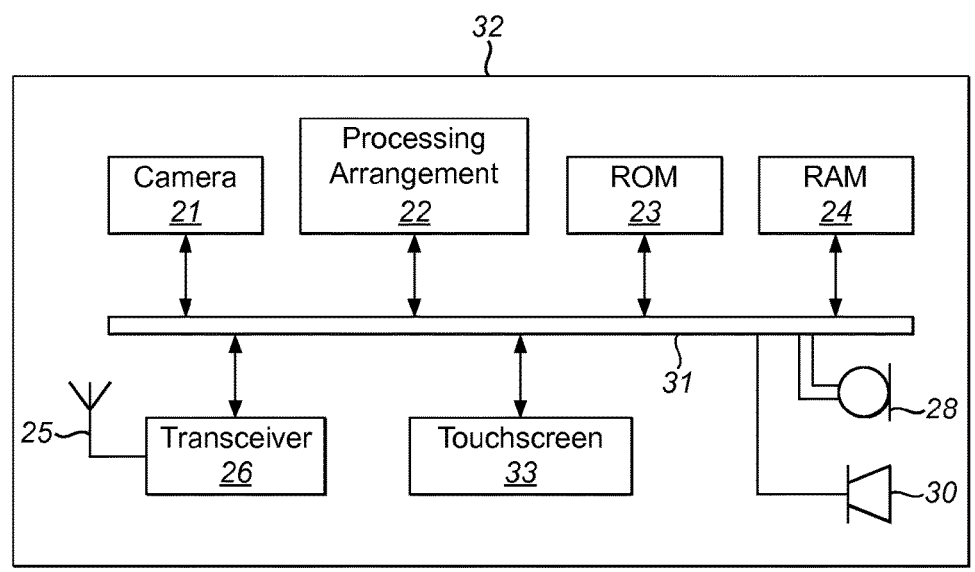
FIG. 2b is a block diagram of a data collection device according to another embodiment.

FIG. 2b is a block diagram of a data collection device according to another embodiment, that may be used to collect data from the injection device 1 of FIG. 1.

In the particular example shown in FIG. 2b, the data collection device is a tablet computer 32. The tablet computer 32 is equipped with a built-in camera 21, a processing arrangement 22 including one or more processors, such as a microprocessor, a Digital Signal Processor (DSP), Application Specific Integrated Circuit (ASIC), Field Programmable Gate Array (FPGA) or the like, together with memory units 23, 24, including a read-only memory 23 and a random access memory 24, which can store software for execution by the processing arrangement 22. The tablet computer 32 also includes communications equipment 25, 26, such as an antenna 25 and a transceiver 26, to permit bi-directional communication with one or more of a cellphone network, a personal area network, a local wireless network and the Internet. In this particular example, the tablet computer 32 further includes a touch-screen 33, which serves as an input arrangement and a display, a speaker 30 and, optionally, a microphone 28. The tablet computer 32 also includes a communications bus 31 allowing for communication between the camera 21, processing arrangement 22, memory units 23, 24, communications equipment 25, 26, touch-screen 33, speaker 30 and, where provided, microphone 28.

In these particular examples, the software stored in the memory units 23, 24 of the cellphone 20 or tablet computer 33 includes software application or "app" that, when executed by the processing arrangement 22, causes the cellphone 20 or tablet computer 33 to take an image of the injection device 1 and process the image to obtain data regarding the type of medicament in the injection device 1 and/or the selected dose. An example method according to an embodiment will now be described with reference to FIGS. 3 to 9.

Figure 3:
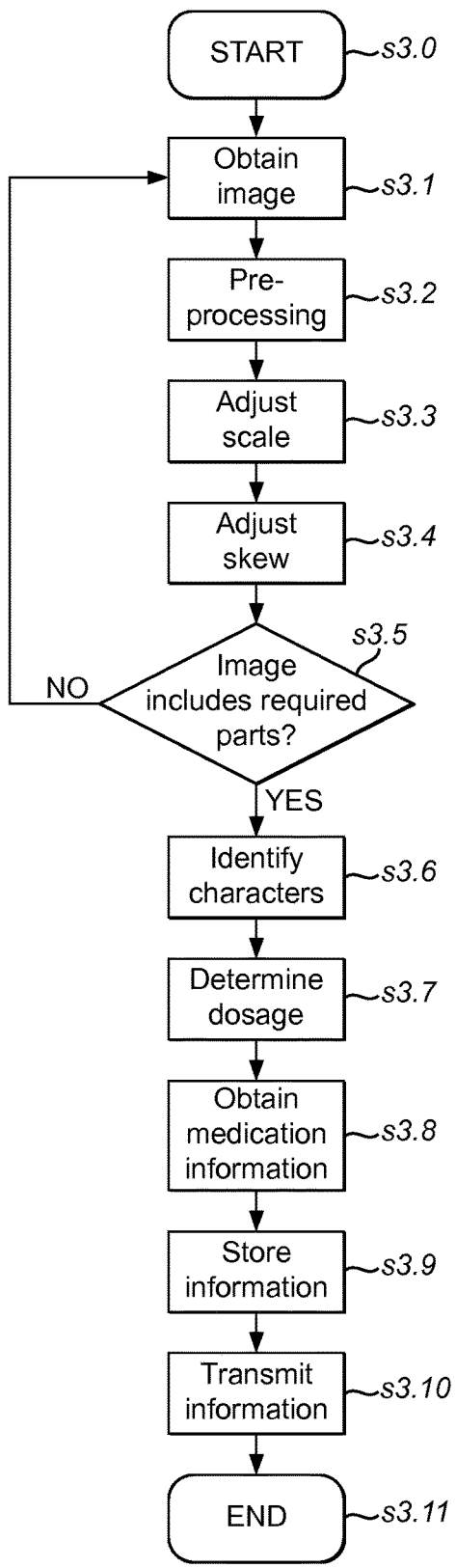
FIG. 3 is a flowchart of a data collection method according to an embodiment.

Starting at FIG. 3, step 3.0, the camera 21 is controlled to take an image of at least the dosage window 13 of the injection device 1 (step s3.1). In some embodiments, the app is configured to cause the processing arrangement 22 to provide guidance to the user before the image is taken, by providing instructions regarding positioning of the injection device 1 relative to the camera 21 based on a "live view" of the field of view of the camera 21. For example, the app may be configured to guide the user to position the camera 21 at a distance at which the camera 21 can obtain a good focus on the dosage window 13. In certain embodiments, such focus may be achieved when the distance between the camera and the injection device 1 is approximately 30 cm.

Further, if medicament information is included only in another part of the injection device 1, such as the label 19, then the app may cause the processing arrangement 22 to instruct a user of the data collection device 20, 33 to include that part of the injection device 1 by providing a message on the display 29 and/or an announcement over the speaker 30.

Optionally, the camera 21 may be controlled by the app to take multiple images of the injection device 1 with different exposure times and the processing arrangement 22 configured to combine the multiple images to provide a high dynamic range ("HDR") image.

In this embodiment, the processing arrangement 22 then performs pre-processing (step s3.2), to assess and, if required, improve image data quality by executing the following steps:
Defective and bad pixel correction
Light correction
Distortion
Jitter For example, an exposure control algorithm rejects pictures that are too bright or too dark and the user instructed to take a new picture so that the exposure parameters can be adjusted. It is noted that the pre-processing is an optional feature. The app may be designed to perform to the required standard without pre-processing of the image.

Alternatively, the app may be configured to cause the processing arrangement to control the exposure parameters or to control additional lighting, for example using a flash unit associated with the camera 21, to provide suitable illumination.

Since the data collection device 20, 32 is hand-held, the distance between the injection device 1 and the camera 21 and the orientation of the dosage window 13 and, where provided, the label 19, relative to the camera 21 are not fixed. In view of this, the processing arrangement 22 adjusts the scale of the image so that the size of the characters displayed within the dosage window 13 are within a predetermined range (step s3.3).

The processing arrangement 22 may further adjust the image by correcting skew of the characters displayed in the dosage window 13 based on the orientation of the injection device 1 relative to the camera and/or any slanting of the characters displayed in the dosage window 13 (step s3.4). For instance, the numbers in the dosage window 13 might be slanted for ease of recognition and positioning by a user, but may be easier to decode by the data collection device 20, 32 if the slant is removed.

The scale and skew adjustments may be based on an analysis of features of the injection device 1 of predetermined shape and/or size. For example, the processing arrangement 22 may identify the dosage window 13, label 19, a logo (not shown) on the injection device 1 and/or other features of the injection device 1 in the image and, based on information regarding the expected shape and/or size of those features, adjust the scale and alignment of the image taken by the camera 21 and correct for skew of text and numbers included in the image.

In some embodiments, the app may also control the processing arrangement 22 to determine whether the dosage window 13 and a particular part of the injection device 1, such as the label 19, that includes medicament information are included in the image (step s3.5). If those parts of the injection device 1 are not included, an instruction is provided to the user to take a new image. The determination may be based on the scale of the injection device 1 in the image and the location of one or more parts of the injection device 1 within the image. Alternatively, in embodiments where a user is guided based on "live view" before taking the image, the app may provide further guidance to the user regarding suitable positioning of the injection device 1 relative to the camera 21 so that the relevant parts of the injection device 1 are within a field of view of the camera 21.

Also in some embodiments (not shown) a 2D Barcode printed beside the window to be read, which contains drug information as drug type, expiration date, batch number. With that no color detection of the pen body is needed.

The processing arrangement 22 then attempts to recognize characters from the image, using Optical Character Recognition (OCR) software included in the app (step s3.6), in order to determine a number or other dosage indication displayed in the dosage window 13 (step s3.7).

Figure 4:
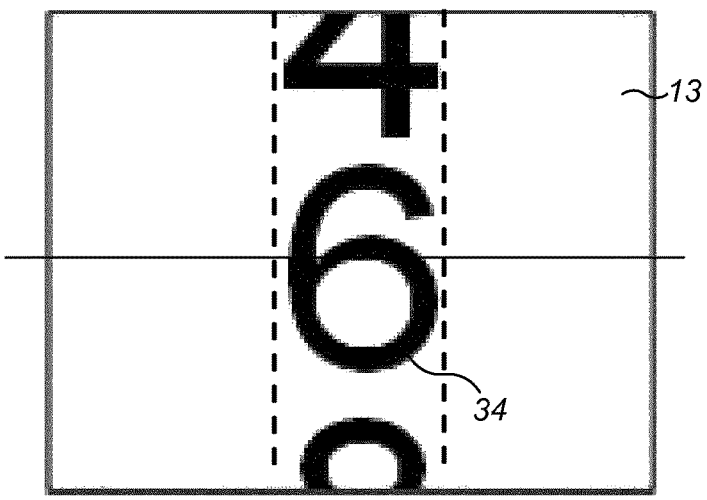
FIGS. 4 and 5 each show a portion of a dosage window of the drug delivery device of FIG. 1a, with examples of digits that may be displayed.
Figure 5:
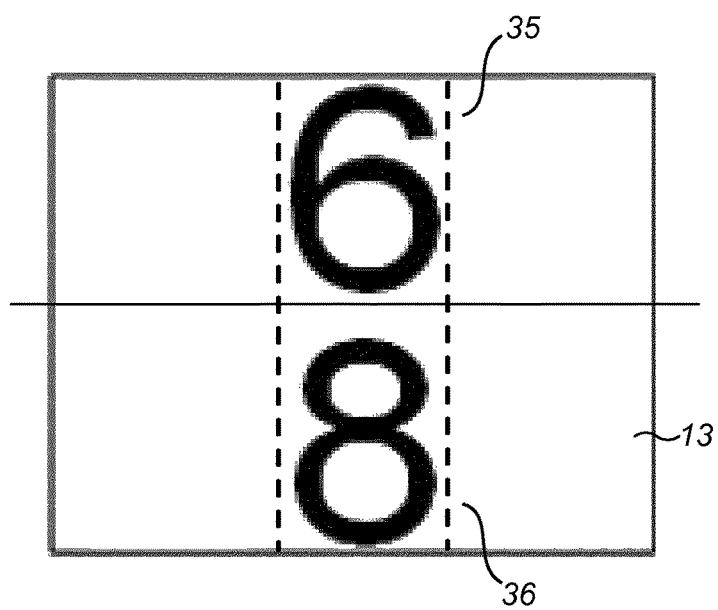

FIGS. 4 and 5 depict a portion of the dosage window 13, showing examples of digits that may be displayed. In FIG. 4, a dosage has been dialed into the injection device 1 such that the a digit 34, in this case the number 6 indicating 6 IU, is displayed centrally in the dose window 13. In FIG. 5, a dosage of 7 IU has been dialed into the injection device 1 such that digits 35, 36, representing the numbers 6 and 8 respectively, are both displayed in the dose window 13 and the space between these numbers occupies the central region of the dose window 13. In this particular embodiment, the processing arrangement 22 is configured to execute an algorithm allowing both of the situations depicted in FIGS. 4 and 5 to be decoded accurately.

The OCR process comprises the steps of:
Binarization
Segmentation
Pattern matching
Position calculation There may, in some embodiments, be two OCR algorithms that are operated in parallel to provide increased reliability of the OCR process. In such embodiments, the two OCR algorithms have the same input image and are intended to provide the same output. They both perform similar steps however the individual methods used in each step may vary. These two OCR algorithms may differ in one of the binarization, segmentation, pattern matching and position calculation steps or in more than one of these steps. Having two OCR-parts which use different methods to provide the same result increases the reliability of the entire algorithm as the data has been processed in two independent ways.

Figure 6:
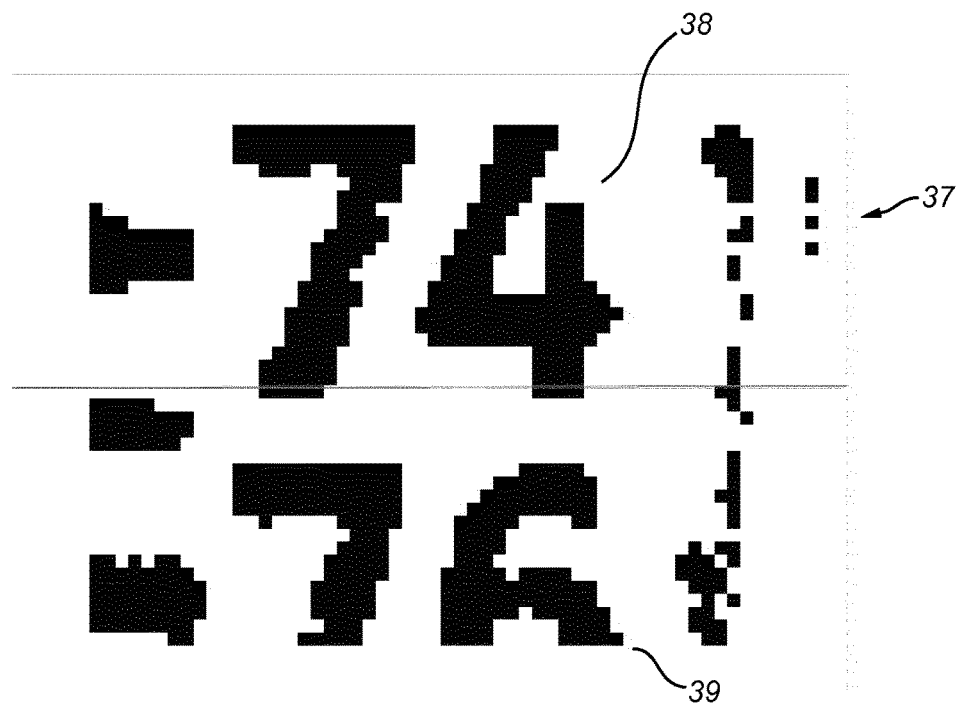
FIG. 6 shows an example of a binarized digits corresponding to digits displayed in the dosage window.
Figure 7:
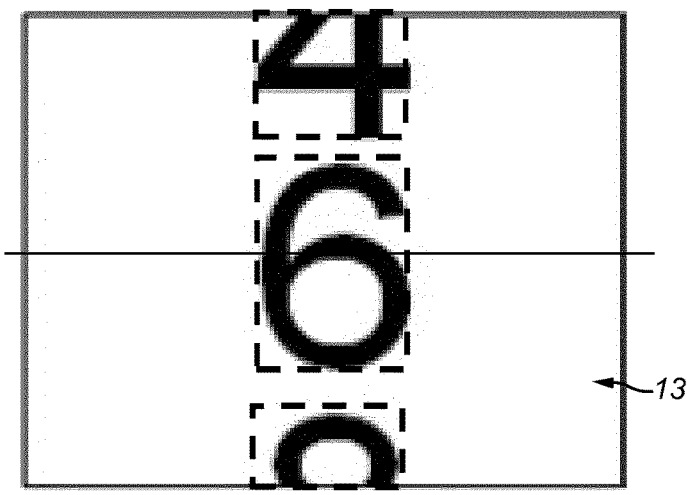
FIGS. 7 and 8 show diagrammatically further examples of digits that may be displayed in the dosage window.
Figure 8:
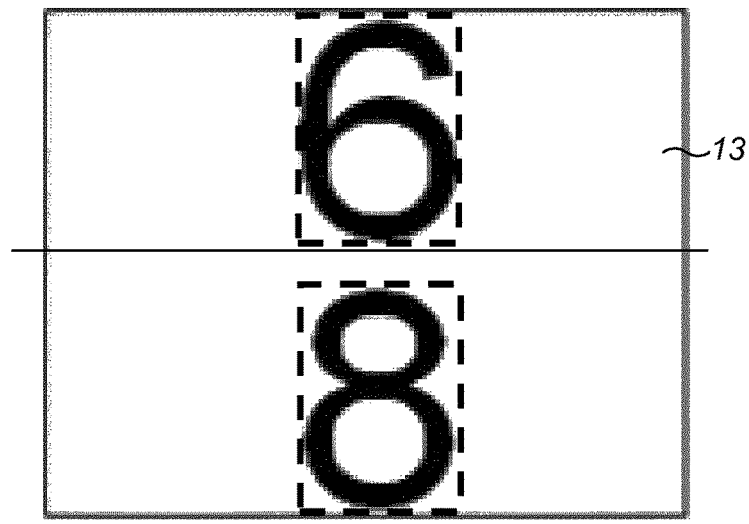

In the OCR process, the color or greyscale image obtained from the camera 21 and adjusted as described above is converted into a purely black and white image 37, such as that depicted in FIG. 6, through a binarization process. In an example where dark numbers are presented on a bright background in the dosage window, the black and white image would indicate the presence of digits 38, 39 with black pixels and the absence of digits with white pixels, as shown in the example of FIG. 6. In some embodiments a fixed threshold is used to separate between black and white pixels. Pixels that have a value at or above the threshold become white, pixels below the threshold become black in the binarized picture. A high threshold will lead to artefacts (black parts in white areas), whereas a low threshold has the risk that in some cases parts of digits are missing. In some embodiments, the threshold is chosen so that in no case are parts of digits are missing because the algorithm is in general robust against artefacts (i.e. an accurate OCR process can be performed in the presence of some artefacts). In tests where an image was analyzed using 256 grey values, a threshold value of 127 showed good results.

The use of a fixed threshold is possible where light correction has been performed, for example, in the pre-processing. The combination of the light correction and the fixed threshold is similar to a windowed mean binarization. A windowed mean binarization compares the pixel-value with the mean value of the pixels of the area where it is located. Performing the light correction step before the distortion and slant correction steps means that more information is available to be used for the OCR process, which has been shown to yield better results on the edges and corners of the picture.

Alternatively, the Otsu threshold method may be applied to the captured greyscale image to produce a binary image similar to the banalized image 37 shown in FIG. 6. In some alternative embodiments, the binarization may be omitted and the OCR part of the algorithm may be performed on the captured color or greyscale image.

Segmentation is then performed. The goal of this part of the algorithm is to determine the exact location of each visible or partly visible number in the image. To achieve this, the algorithm defines the boundaries of the visible digits by finding the edges of the digits. This is generally accomplished in two steps, which may be performed in any order. Referring again to FIGS. 4 and 5, the processing arrangement 22 may perform a "vertical projection" in which the pixel columns making up the binarized image 37 are analyzed. Each pixel column is analyzed individually and the sum of the number of black pixels in each column is computed. In some embodiments, only a pixel column having zero black pixels defines the edge of a number. Alternatively, a low threshold for the number of black pixels may be set to account for dirt, scratches and other disturbances. Difference values for adjacent columns are calculated and the boundary having the greatest difference represents the edge of the number. Additionally, the pixel content of overlapping groups of columns (e.g. three adjacent columns) may be calculated to aid in determining the horizontal edges of the numbers.

The processing arrangement then performs a "horizontal projection" in which the pixel rows making up the binarized image 37 are analyzed. This proceeds in a similar manner to that as described above with regard to the vertical projection.

The expected result of the horizontal projection is added to that of the vertical projection such that the edges of the visible numbers are identified. The processing arrangement 22 may be pre-programmed with the expected height (in pixel rows) of a full number, and so is able to recognize the presence of partially visible numbers.

In another embodiment, the "horizontal projection" and the "vertical projection" may be based on an analysis where the sum of white pixels is computed, provided that the expected number of white pixels in each row and column is known.

Knowing the exact location allows for using only the part of the image which represents the visible number or numbers for the next steps in the OCR process. By this any impact of other objects besides the number, e.g. dirt, scratches and other disturbances, can be reduced. Further, the total number of pixels to be processed in subsequent steps, e.g. in the pattern matching step, is also reduced. This helps reducing resource requirements. This also helps increasing performance. In addition, knowing the exact location also supports determining the vertical position relative to the center of the image.

The next step in the OCR process is to select one of the visible numbers to be decoded and identified. This is done by designating one of the numbers as the "primary digit row". The primary digit row is selected based on which visible number has the greatest height. This is because all of the numbers printed on the sleeve 70 have approximately the same height and it can be assumed that the number having the greatest height will be fully visible and therefore easy to decode with a high degree of certainty. In the example shown in FIG. 7, the number "6" has a greater height than the partially visible numbers above and below and so is selected as the primary digit row. In the example shown in FIG. 8, both the numbers "6" and "8" are fully visible and have the same height. In this case, the uppermost number is selected as the primary digit row. The primary digit row is the number which is subsequently used to determine the dose dialed into the injection device 1.

A standard injection device 1 for self administration of insulin can inject any number of units of medicament from 1 to 80 IU. Therefore, in order to properly decode the number identified as the primary digit row, it must be determined whether the number consists of one or two digits. The processing arrangement 22 therefore performs a series of steps in order to determine whether each number consists of one or two digits, and in the latter case, to separate the digits from each other. The processing arrangement 22 may use the column pixel information previously calculated for this purpose. In the example shown in FIG. 9, a dosage of 9 IU of medicament has been dialed into the injection device 1. The expected results of the horizontal and vertical projections are shown. The number "10" is of greater height than the number "8" and is therefore selected as the primary digit row.

After this the processing arrangement 22 determines whether the selected primary digit row is wider than a pre-defined "maximum digit width" value. The processing arrangement 22 may be pre-programmed with information relating to the expected size of the numbers in the captured images, so that a maximum expected width for a single digit can be defined. In order to increase reliability, the maximum width may be set as a small number of pixel columns more than the widest number. If the width of the primary digit row is the maximum digit width or less, it is assumed that the row contains a single digit. If the primary digit row is too wide to be a single digit, then a second vertical projection is then performed on the primary digit row (rather than on the whole image). In addition, the expected width of each individual digit may be used to predict the point at which the separation should occur.

Figure 9:
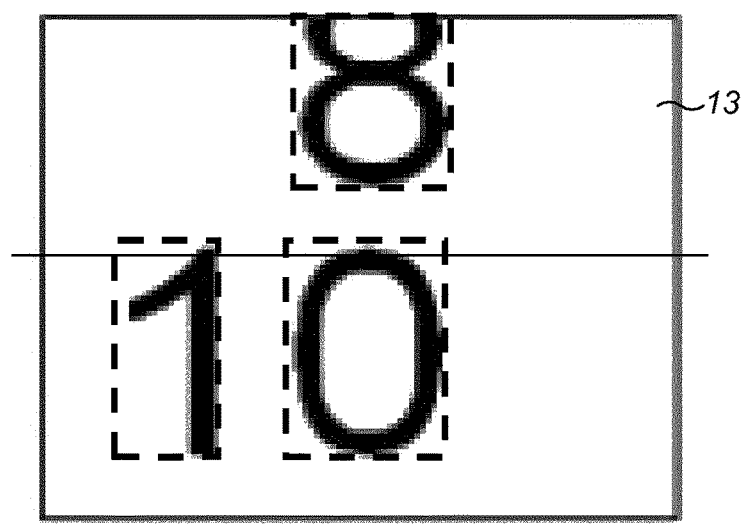
FIG. 9 shows a further example of digits that may be displayed in the dosage window where a primary digit row contains two digits.

The exemplary field of view 900 shown in FIG. 9 is a diagrammatic representation in which the numbers are well spaced. In other arrangements, the numbers may be displayed quite close together in the dosage window, owing to limited available space and the need for the numbers to be readable to a user. Thus, after binarization, the two digits making up the number may not be cleanly separated, i.e. there may not be a column having no black pixels between the two digits. This is the case in the exemplary binarized image shown in FIG. 6, in which the "7" and "4" of the upper digits 37 do not have a pixel column between them containing no black pixels. In this case, the expected width of each individual digit is again used to predict the point at which the separation should occur. If the predicted column contains black pixels, then the deviations of this column from adjacent columns are calculated to determine the best separation point. In this situation, as it is not clear whether the black pixels in the chosen separating column belong to the left or right digit, they are ignored. This has been shown to have a minimal effect on the reliability of the OCR process to correctly identify the digits.

A pattern matching process is then performed to identify the digits in the primary digit row. Templates for each number may be pre-programmed via the app and the identified digits may then be compared to these templates. In a straight forward approach the pattern matching could be performed on a pixel-by-pixel basis. However, this may require high computing power and may be prone to position variation between the image and the template. Where templates are used, the app may be configured to cause the processing arrangement 22 to perform other types of manipulation on the images numbers, for example by changing the size of one or more digits, cropping the numbers to a defined pixel area and shearing numbers printed in a italic font into an upright position. These manipulations may be performed before a pattern matching comparison with the stored templates. Alternatively, these manipulations may be performed in preprocessing before the binarization process. Additional shading, distortion and exposure correction may also be performed.

In some other embodiments, a feature recognition process is performed. Features may be horizontal, vertical or diagonal lines, curves, circles or closed loops etc. Such features may be recognized in the image of the selected number and compared with templates.

In yet further embodiments, the pattern matching algorithm may be based on a vector comparison process. For example, the templates may be in the form of vectors describing the position and length of each line (continuous run) of black pixels. In one example, the position and length relate to the absolute position in the respective line. In another example, the position and length relate to a vertical line extending through the center of the template. The captured binary image of each digit may similarly be converted into vectors and compared with each stored template in turn to find the best match. When comparing the vectors of the captured image with a particular digit template, any deviations result in a penalty being applied for the likelihood of a match between the image and that template. The magnitude of the penalty may depend on the number of missing or extra black pixels in the image compared to the template. After the digit image has been compared with each template and all of the penalties have been applied a decision is made as to which digit is present. In good optical conditions, the correct template will have a very low penalty, while all other templates will have a high penalty. If the primary digit row consists of two digits, this process is performed on both digits and the processing arrangement 22 can then combine the outcomes to produce a final result for the number.

Special measures may exist for certain digits. For example, "1" deviates substantially in width from all other digits resulting in common misdetections. To counter this, if a binary image of a digit is wider than the expected width of "1", then it receives an additional detection penalty when being compared with the stored vector template of "1".

In some exceptional cases, if the confidence level in the result of the pattern matching of the primary digit row is below a certain threshold (e.g. 99%), then the processor may perform a second pattern matching process on one or more of the other visible or partially visible numbers. Since the order of the numbers is known, this second pattern matching can act as a check that the first pattern matching returned the correct result.

If the confidence level in the result is still not high enough, then an instruction may be presented to the user to obtain a second image and steps s3.1 to s3.6 repeated. Alternatively, an error message may be displayed.

Once the digit or digits of the primary digit row have been successfully identified, a weighting function is applied in order to determine a dose dialed into the injection device 1. To formulate the weighting function, the vertical position of the primary digit row relative to the center of the dosage window 13 may be determined. This may be done by calculating the offset of the middle pixel row comprising the primary digit row relative to a pixel row representing a center line of the dosage window 13 in the image.

For example, in some embodiments the optical sensor comprises a rectangular 64×48 array of photosensitive elements. The resulting binary image is a pixel array having these same dimensions. The $24^{th}$ and/or $25^{th}$ pixel row may be designated as the central row of the image. The position of the middle pixel row comprising the primary digit row is determined. The offset, in pixel rows, between the middle pixel row comprising the primary digit row and the central row or rows of the image is then calculated. This offset may be positive or negative depending on the direction of the offset. The offset is converted into a fraction by dividing it by the distance (in pixel rows) between successive numbers before being applied to the determined numbers accordingly. The offset therefore allows for determining the rotational position of the number relative to the sensor. If the central pixel row of the primary digit row is the same as the central pixel row of the image, then the offset is zero and the position is equal to the primary digit row number. However, there is likely to be some offset in most circumstances.

The distance between successive numbers printed on the numbered sleeve 70 is constant, since the numbers represent a dose which is related to a discrete mechanical movement of the injection device mechanism. Therefore, the distance (in pixel rows) between successive numbers in the captured image should also be constant. The expected height of the numbers and spaces between the numbers may be pre-programmed into the app. As an example, the expected height of each numbers may be 22 pixels and the expected height of the spaces between the numbers may be 6 pixels. Therefore, the distance between the central pixel rows of successive numbers would be 28 pixels.

Continuing this example, if the pixel rows are numbered sequentially from the top to the bottom of the image, the application of the weighting function may be defined mathematically as:

Position=primary digit row number+[2×offset/(expected height of number+expected height of space)]

Where offset=image row number corresponding to the center of the dosage window−primary digit row central row number Thus, if the primary digit row is in the upper half of the image, then the offset is positive and if the primary digit row is in the lower half of the image, then the offset is negative. For example, if the number shown in the primary digit row is "6" and the offset is zero, then the calculated position would be:

Position=6+[2×0/(28)]=6

Thus a result of "6" would be returned as expected.

In another example, where 75 IU are dialed into the injection device 1, if the top number, "74", is selected as the primary digit row and there is a positive offset of 11 pixel rows according to the equation above, and again assuming a combined number/space height of 28 pixels, the calculated position would be:

Position=74+[2×11/(28)]=74.79

This result is then rounded up to the nearest whole number, to give a position determination of "75" as expected.

The skilled person will appreciate that the above described weighting function and position determination represents only one example and that numerous other calculation methods may be used to arrive at the same result. The skilled person would also appreciate that the above described mathematical calculation may be modified and improved to reduce the computation time. Thus the exact form of the weighting function is not essential to a definition of the present disclosure.

In some injection devices, due to space restrictions and the need for the numbers to be of a certain size, only even numbers are presented in the dosage window 13. In some other injection devices, only odd numbers may be displayed. However, any number of units of medicament can be dialed into the injection device 1. In other injection devices, both even and odd numbers may be presented and it may be possible to dial half-unit doses into the injection device. The injection device may be limited to a maximum dialed dose of 80 IU. Alternatively, only every $3^{rd}$, $4^{th}$ or $5^{th}$ number may be displayed and doses between the numbers may be indicated by tick marks. In view of this, the app may include instructions for controlling the processing arrangement 22 to identify the numbering sequence used in the injection device 1. For example, the user may be prompted to enter information regarding the injection device 1 via a keypad 27 or touch-screen 33 or information obtained from the image, for example from the text or a barcode on the label 19 may be used. The app may include a look-up table or other information indicating the numbering sequences used for various injection devices 1. The processing arrangement 22 may then determine the selected dose based on both OCR data and the appropriate numbering sequence for the injection device 1. Alternatively, or additionally, a modified form of the weighting function may be used, as the height of the numbers and size of the space between the numbers may also be modified.

The method may optionally include post-processing, such as performing sanity checks and hysteresis calculations. Alternatively, the result of the OCR process may be finalized without post-processing.

Information regarding the type of medicament may be obtained by one or more of using OCR from a part of the image including the label 19, extracting and interpreting a barcode from a part of the image including the label 19 or by identifying a color of a part of the injection device 1 that indicates the medicament type from the image (step s3.8).

In embodiments where color detection is used, the numbered sleeve 70 of the injection device 1 may be configured to provide reference color information to allow one or more colors in the image to be identified correctly. For example, the background of the printed numbers may be used to provide a white balance level for calibrating the colors of the components of the injection device 1 as shown in the image.

The information obtained from the image may then be stored in the random access memory 24 of the data collection device 20, 32 (step s3.9) and/or transmitted to another device via a network, such as a cellphone network, personal area network or the Internet, using the communications equipment 25, 26 (step 3.10). Optionally, information regarding a timestamp of the image may also be stored and/or transmitted. In this manner, the administration of medicament to a patient may be recorded and monitored.

As shown by the embodiments discussed above, the provision of an app or similar software product to obtain information regarding an injection, other medical treatment or the operation of other equipment may permit more accurate and/or reliable recording of such information using a device such as a cellphone 20 or tablet 32 that is commonly available and familiar to the user. Since the embodiments described above do not require the manufacture and distribution of a specialized device, they may, potentially, reduce the costs and complexity of providing recordal and/or monitoring of treatment or operations.

While the embodiments above have been described in relation to collecting data from an insulin injector pen, it is noted that embodiments may be used for other purposes, such as monitoring of injections of other medicaments or other medical processes. Embodiments may also be used to for non-medical purposes, for example, in monitoring the operation of other types of equipment for safety reasons.

The invention claimed is:

1. A method of recording a medicament dose using a handheld data collection device, the method comprising:
    capturing, by a camera of the handheld data collection device positioned at a distance from a medicament dose indicator of a medicament delivery device, an image of the medicament dose indicator, wherein the distance between the camera and the medicament dose indicator is variable;
    adjusting a scale of said image;
    adjusting said image for skew of one or more characters displayed by the medicament dose indicator;
    determining a position of at least one of said one or more characters in the image;
    identifying the at least one character using optical character recognition; and
    determining a medicament dose indicated by the medicament dose indicator based on a result of said optical character recognition.

2. A method according to claim 1, wherein said handheld electronic device is a cellphone or a tablet computer.

3. A method according to claim 1, wherein capturing an image comprises combining multiple images captured by said camera having different exposure levels, to provide said image with a high dynamic range.

4. A method according to claim 1, comprising obtaining color information from said image and identifying a type of medicament to be dispensed based on said color information.

5. A method according to claim 4, wherein obtaining color information comprises obtaining a color balance measurement based on reference color information provided on the medicament delivery device.

6. A method according to claim 1, wherein said medicament delivery device is an injector pen comprising a movable component for selecting said medicament dose to be dispensed.

7. A computer program comprising computer-readable instructions that, when executed by a processor, causes a method according to claim 1 to be performed.

8. An application for one or both of a smartphone and a tablet computer, wherein said application comprises a computer program according to claim 7.

9. A handheld data collection device comprising:
    a camera; and
    a processing arrangement configured to:
        capture an image of a medicament dose indicator of a medicament delivery device using said camera when the camera is positioned at a distance from the medicament dose indicator, wherein the distance between the camera and the dose indicator is variable;
        adjust a scale of said image;
        adjust said image for skew of one or more characters displayed by the medicament dose indicator;
        determine a position of at least one of said one or more characters in the image;
        identify the at least one character using optical character recognition; and
        determine a medicament dose indicated by said medicament dose indicator based on a result of said optical character recognition.

10. A data collection device according to claim 9, wherein said handheld electronic device is a cellphone or a tablet computer.

11. A data collection device according to claim 9, wherein said processing arrangement is configured to combine multiple images captured by said camera, said multiple images having different exposure levels, to provide said image with a high dynamic range.

12. A data collection device according to claim 9, wherein said processing arrangement is configured to identify a color of at least one component of the medicament delivery device and to determine a type of said medicament dose based on said color.

13. A method of recording a medicament dose using a handheld data collection device, the method comprising:
    capturing, by a camera of the handheld data collection device, an image of a medicament dose indicator of a medicament delivery device;
    adjusting a scale of said image;
    adjusting said image for skew of one or more characters displayed by the medicament dose indicator by removing slanting of the one or more characters;
    determining a position of at least one of said one or more characters in the image;
    after adjusting said image for skew by removing slanting of the one or more characters, identifying the one or more characters using optical character recognition; and
    determining a medicament dose indicated by the medicament dose indicator based on a result of said optical character recognition.

14. A method according to claim 13, wherein said camera of said handheld data collection device is positioned at a distance from the medicament dose indicator of the medicament delivery device, wherein the distance between said camera and said medicament dose indicator is not fixed.

15. A method according to claim 13, wherein said handheld electronic device is a cellphone or a tablet computer.

16. A method according to claim 13, wherein capturing an image comprises combining multiple images captured by said camera having different exposure levels, to provide said image with a high dynamic range.

17. A method according to claim 13, comprising obtaining color information from said image and identifying a type of medicament to be dispensed based on said color information.

* * * * *